US011226327B2

(12) United States Patent
Brown et al.

(10) Patent No.: US 11,226,327 B2
(45) Date of Patent: Jan. 18, 2022

(54) LINEAR, CARTRIDGE-BASED GLUCOSE MEASUREMENT SYSTEM

(71) Applicant: ASCENSIA DIABETES CARE HOLDING AG, Basel (CH)

(72) Inventors: Daniel Brown, Edwardsburg, MI (US); Martin Antoine Mathelier, Garnerville, NY (US); Sung-Kwon Jung, Granger, IN (US)

(73) Assignee: Ascensia Diabetes Care Holdings AG, Basel (CH)

( * ) Notice: Subject to any disclaimer, the term of this patent is extended or adjusted under 35 U.S.C. 154(b) by 597 days.

(21) Appl. No.: 15/076,278

(22) Filed: Mar. 21, 2016

(65) Prior Publication Data

US 2016/0202236 A1   Jul. 14, 2016

Related U.S. Application Data

(63) Continuation of application No. 14/366,914, filed as application No. PCT/US2012/070270 on Dec. 18, 2012, now Pat. No. 9,417,229.

(60) Provisional application No. 61/577,859, filed on Dec. 20, 2011.

(51) Int. Cl.
*G01N 33/487* (2006.01)
*A61B 5/145* (2006.01)

(52) U.S. Cl.
CPC . *G01N 33/48778* (2013.01); *G01N 33/48757* (2013.01); *A61B 5/14532* (2013.01); *B01L 2200/04* (2013.01); *B01L 2300/04* (2013.01); *B01L 2300/0809* (2013.01); *B01L 2300/0858* (2013.01); *B01L 2300/123* (2013.01)

(58) Field of Classification Search
CPC ........ G01N 33/48778; G01N 33/45757; B01L 9/00; A61B 5/14532
See application file for complete search history.

(56) References Cited

U.S. PATENT DOCUMENTS

| 4,217,331 A | 8/1980 | Schaub |
| 4,223,524 A | 9/1980 | Nakagawa |
| 4,328,184 A | 5/1982 | Kondo |

(Continued)

FOREIGN PATENT DOCUMENTS

| CN | 1427256 A | 7/2003 |
| CN | 1501788 A | 6/2004 |

(Continued)

OTHER PUBLICATIONS

Definition of Linear: https://www.collinsdictionary.com/us/dictionary/english/linear (Year: 2018).*

(Continued)

*Primary Examiner* — Matthew D Krcha
(74) *Attorney, Agent, or Firm* — Dugan & Dugan, PC

(57) ABSTRACT

A test sensor container for use with an analyte measuring system may include a cartridge that includes a base, two opposite sidewalls extending away from the base, and a plurality of compartments each dimensioned to hold a test sensor. At least one of the two opposite sidewalls is oriented at an acute angle relative to a reference axis that is perpendicular to the base. The test sensor container may further include at least one foil cover sealing the plurality of compartments and an ejection mechanism.

20 Claims, 7 Drawing Sheets

(56) References Cited

U.S. PATENT DOCUMENTS

| | | |
|---|---|---|
| 5,120,420 A | 6/1992 | Nankai et al. |
| 5,194,393 A | 3/1993 | Hugl et al. |
| 5,510,266 A | 4/1996 | Bonner et al. |
| 5,575,403 A | 11/1996 | Charlton et al. |
| 5,630,986 A | 5/1997 | Charlton et al. |
| 5,632,410 A | 5/1997 | Moulton et al. |
| 5,645,798 A | 7/1997 | Schreiber et al. |
| 5,660,791 A | 8/1997 | Brenneman et al. |
| 5,720,924 A | 2/1998 | Eikmeier et al. |
| 5,738,244 A | 4/1998 | Charlton et al. |
| 5,759,364 A | 6/1998 | Charlton et al. |
| 5,798,031 A | 8/1998 | Charlton et al. |
| 5,810,199 A | 9/1998 | Charlton et al. |
| 5,854,074 A | 12/1998 | Charlton et al. |
| 5,856,195 A | 1/1999 | Charlton et al. |
| 5,863,800 A | 1/1999 | Eikmeier et al. |
| 6,428,664 B1 | 8/2002 | Bhullar et al. |
| 6,478,158 B2 | 11/2002 | Gaffney |
| 6,497,845 B1 | 12/2002 | Sacherer |
| 6,534,017 B1 | 3/2003 | Bottwein et al. |
| 6,827,899 B2 | 12/2004 | Maisey et al. |
| 6,988,996 B2 | 1/2006 | Roe et al. |
| 6,997,343 B2 | 2/2006 | May et al. |
| 7,138,089 B2 | 11/2006 | Aitken et al. |
| 7,198,606 B2 | 4/2007 | Boecker |
| 7,211,096 B2 | 5/2007 | Kuhr et al. |
| 7,264,139 B2 | 9/2007 | Brickwood et al. |
| 7,270,247 B2 | 9/2007 | Charlton |
| 7,364,699 B2 | 4/2008 | Charlton |
| 7,449,148 B2 | 11/2008 | Matsumoto et al. |
| 7,549,323 B2 | 6/2009 | Charlton et al. |
| 7,604,592 B2 | 10/2009 | Freeman et al. |
| 7,790,106 B2 | 9/2010 | Uchigaki et al. |
| 7,913,838 B2 | 3/2011 | Zhong |
| 8,105,536 B2 | 1/2012 | Charlton |
| 8,124,014 B2 | 2/2012 | Charlton |
| 8,158,078 B2 | 4/2012 | Chan et al. |
| 8,296,918 B2 | 10/2012 | Alden et al. |
| 8,372,016 B2 | 2/2013 | Freeman et al. |
| 8,574,510 B2 | 11/2013 | Gofman et al. |
| 9,097,700 B2 | 8/2015 | Brown et al. |
| 9,204,829 B2 | 12/2015 | Prais et al. |
| 2002/0057993 A1 | 5/2002 | Maisey et al. |
| 2002/0076349 A1 | 6/2002 | Aitken et al. |
| 2003/0223906 A1 | 12/2003 | McAllister et al. |
| 2004/0178216 A1* | 9/2004 | Brickwood ...... G01N 33/48757 221/268 |
| 2005/0201897 A1 | 9/2005 | Zimmer |
| 2005/0245954 A1 | 11/2005 | Roe et al. |
| 2006/0182656 A1 | 8/2006 | Funke et al. |
| 2007/0007183 A1 | 1/2007 | Schulat |
| 2007/0119710 A1 | 5/2007 | Goldberger et al. |
| 2007/0173739 A1 | 7/2007 | Chan |
| 2007/0173740 A1 | 7/2007 | Chan et al. |
| 2008/0093235 A1 | 4/2008 | Zhong et al. |
| 2008/0094804 A1 | 4/2008 | Reynolds et al. |
| 2008/0118399 A1 | 5/2008 | Fleming |
| 2008/0131322 A1* | 6/2008 | Kheiri ............ G01N 33/48757 422/82.01 |
| 2008/0164164 A1 | 7/2008 | Zhong |
| 2008/0164280 A1 | 7/2008 | Kuriger et al. |
| 2008/0181818 A1 | 7/2008 | Ruan |
| 2008/0190766 A1 | 8/2008 | Rush et al. |
| 2009/0035120 A1 | 2/2009 | List |
| 2009/0074617 A1* | 3/2009 | Uchigaki ................ B01L 9/52 422/68.1 |
| 2009/0314106 A1 | 12/2009 | Van Halsema |
| 2010/0041156 A1 | 2/2010 | Brenneman et al. |
| 2010/0087754 A1 | 4/2010 | Rush et al. |
| 2010/0129900 A1 | 5/2010 | Clark et al. |
| 2010/0291588 A1 | 11/2010 | McDevitt et al. |
| 2012/0082597 A1 | 4/2012 | Doniger et al. |
| 2013/0048495 A1 | 2/2013 | Charlton |
| 2013/0324822 A1 | 12/2013 | Prais et al. |
| 2015/0004059 A1 | 1/2015 | Brown et al. |
| 2015/0144484 A1 | 5/2015 | Reynolds |
| 2015/0301016 A1 | 10/2015 | Brown et al. |
| 2016/0025638 A1 | 1/2016 | Charlton |

FOREIGN PATENT DOCUMENTS

| | | |
|---|---|---|
| CN | 101002091 A | 7/2007 |
| CN | 101583306 A | 11/2009 |
| CN | 101583393 A | 11/2009 |
| EP | 1321769 | 6/2003 |
| EP | 1726950 | 11/2006 |
| EP | 1726951 | 11/2006 |
| EP | 2426493 | 3/2012 |
| EP | 2466304 A1 | 6/2012 |
| JP | S54-033797 | 3/1979 |
| JP | S56-175756 | 12/1981 |
| JP | H06-308115 | 11/1994 |
| JP | H0921811 A | 1/1997 |
| JP | 2002-310972 | 10/2002 |
| JP | 2003-028794 | 1/2003 |
| JP | 2003-302314 | 10/2003 |
| JP | 2004-4046 A | 1/2004 |
| JP | 2006-516328 | 6/2006 |
| JP | 2006-517651 | 7/2006 |
| JP | 2007-535388 | 12/2007 |
| JP | 2007-537454 | 12/2007 |
| JP | 2008-001428 | 1/2008 |
| JP | 2008-502901 | 1/2008 |
| JP | 2008-504532 | 2/2008 |
| JP | 2008-544266 | 12/2008 |
| JP | 2012-001256 | 1/2012 |
| KR | 20060105904 A | 10/2006 |
| WO | WO 95/13531 | 5/1995 |
| WO | WO 2001-023885 | 4/2001 |
| WO | WO2001/063272 | 8/2001 |
| WO | WO 2002-008753 | 1/2002 |
| WO | WO 2002-018940 | 3/2002 |
| WO | WO 2003-042691 | 5/2003 |
| WO | WO 2003/069326 | 8/2003 |
| WO | WO 2004-063747 | 7/2004 |
| WO | WO 2005-046477 | 5/2005 |
| WO | WO 2006-002432 | 1/2006 |
| WO | WO 2006-019665 | 2/2006 |
| WO | WO 2006-044850 | 4/2006 |
| WO | WO 2006-065754 | 6/2006 |
| WO | WO 2006-076721 | 7/2006 |
| WO | WO 2007-085438 | 8/2007 |
| WO | WO 2007-147494 | 12/2007 |
| WO | WO 2008-111937 | 9/2008 |
| WO | WO 2009-120664 | 10/2009 |
| WO | WO 2014/164279 | 10/2014 |

OTHER PUBLICATIONS

Taiwan Search Report of Taiwanese Application No. 104106105 dated Aug. 8, 2016.
Supplementary Partial European Search Report of European Application No. 12859868.7 dated Aug. 5, 2015.
International Search Report and Written Opinion of International Application No. PCT/US2012/070270 dated Feb. 26, 2013.
Taiwan Search Report of Taiwanese Application No. 101148835 dated Oct. 6, 2014.
International Preliminary Report on Patentability of International Application No. PCT/US2012/070270 dated Jul. 3, 2014.
International Search Report and Written Opinion of International Application No. PCT/US2014/021691 dated Sep. 10, 2014.
International Preliminary Report on Patentability of International Application No. PCT/US2014/021691 dated Sep. 24, 2015.
International Search Report and Written Opinion of Application No. PCT/US2012/072118 dated Mar. 28, 2013.
International Search Report and Written Opinion of Application No. PCT/US2013/030897 dated Jun. 27, 2013.
Prais et al., of U.S. Appl. No. 14/943,416, titled "Multistrip Cartridge," filed Nov. 17, 2015.
International Preliminary Report on Patentability of Application No. PCT/US2013/030897 dated Dec. 2, 2014.

(56) References Cited

OTHER PUBLICATIONS

International Preliminary Report on Patentability of Application No. PCT/US2012/072118 dated Dec. 11, 2014.
European Office Action and Search Report of European Application No. 13797254.3 dated Dec. 16, 2015.
European Extended Search Report of European Application No. EP15198651.0 dated Feb. 11, 2016.
European Extended Search Report of European Application No. 13797254.3 dated Mar. 21, 2016.
European Extended Search Report of European Application No. 17198856.1 dated Nov. 27, 2017.
Chinese Search Report of Chinese Application No. 201610937322.8 dated Oct. 25, 2018.

* cited by examiner

LINEAR, CARTRIDGE-BASED GLUCOSE MEASUREMENT SYSTEM

CROSS-REFERENCE TO RELATED APPLICATIONS

This is a continuation of U.S. patent application Ser. No. 14/366,914, filed Jun. 19, 2014, now U.S. Pat. No. 9,417,229, issued Aug. 16, 2016, which is a U.S. National Phase of PCT/US12/70270, filed Dec. 18, 2012, which claims the benefit of U.S. Prov. Appln. No. 61/577,859, filed Dec. 20, 2011, the disclosures of which are hereby incorporated by reference herein for all purposes.

BACKGROUND OF THE INVENTION

The present disclosure generally relates to systems and methods for evaluating analytes and, more particularly, to analyte measurement systems designed to detect and measure analytes, such as blood glucose, in a fluid sample.

Conventional analyte measuring systems employ test sensors or test strips for analyzing body fluids, such as blood. Each test strip has a reaction zone containing a reagent. This reagent reacts with an analyte (e.g., blood glucose) and produces a measurable signal indicative of the presence or concentration of said analyte.

The quantitative determination of analytes in body fluids has become a great tool in the diagnosis of certain physiological abnormalities. For example, blood glucose, lactate, cholesterol, and bilirubin are often monitored in individuals. In particular, patients suffering from various forms of diabetes must frequently monitor their blood glucose concentration levels to determine whether any corrective action needs to be taken. For instance, a patient that has detected an irregularly high glucose concentration level may use insulin to lower the blood glucose concentration. Failure to take the appropriate corrective action may result in serious adverse health effects on the individual. For this reason, it is important that measuring systems be accurate and dependable, while preferably also being easy for an individual to use.

While a number of analyte measuring devices have been developed over the years, improvements are still possible. For instance, test sensors are sensitive to the effects of ambient humidity. To control the humidity levels, analyte measuring devices usually include desiccant material. Desiccant material, however, is sometimes not sufficient and the test sensors may also be sealed with a cover, such as a foil, to contain the environment in and around the desiccants and test sensor. Still further improvements would be beneficial.

BRIEF SUMMARY OF THE INVENTION

The present disclosure relates to test sensor containers for use with analyte meters.

The present disclosure relates to test sensor containers for use with an analyte measuring system. In one embodiment, the test sensor container generally includes a cartridge, at least one foil cover, and an ejection mechanism. The cartridge includes a plurality of compartments arranged linearly along a longitudinal axis. Each compartment is dimensioned to hold a test sensor. The foil cover seals the plurality of compartments. The ejection mechanism is configured to break the foil cover to open only one compartment at a time without opening the remaining compartments of the plurality of compartments. As discussed above, the test sensor container may include only a single foil cover. The test sensors may be stored in the plurality of compartments and are arranged side by side along a length of the cartridge extending along a longitudinal axis.

In another embodiment of the present disclosure, the test sensor container includes a cartridge including a plurality of stacked individual compartments connected to one another in an accordion-style fashion, each individual compartment being collapsible from an expanded to a collapsed condition and dimensioned to hold a to sensor when in the expanded condition; at least one foil cover sealing the plurality of compartments; and an ejection mechanism configured to break the at least one foil cover to open only one compartment at a time without opening the remaining compartments of the plurality of compartments. The test sensor container may only include a single foil cover. The test sensor may further include desiccant material inside each of the plurality of compartments.

The present disclosure also relates to analyte measuring systems. In one embodiment, the analyte measuring system generally includes a housing, at least one foil cover, and an ejection mechanism. The housing has a cavity for holding a linear cartridge. The linear cartridge includes a plurality of compartments. Each compartment is adapted to hold a test sensor. The foil cover seals the plurality of compartments. The ejection mechanism is adapted no eject one of the plurality of test sensors from the linear cartridge and includes a flexible blade movable between a first position, where no portion of the flexible blade is located within at least one compartment of the plurality of compartments, and a second position, where at least a portion of the flexible blade is positioned within at least one compartment of the plurality of compartments to open only one compartment at a time without opening the remaining compartments of the plurality of compartments. The analyte measuring system may further include desiccant material inside each of the plurality of compartments.

In another embodiment, the analyte measuring system includes a housing having a cavity for holding a linear cartridge, the linear cartridge defining a longitudinal axis and including a plurality of compartments, each compartment being adapted to hold a test sensor, each test sensor being configured to detect and measure an analyte in a fluid sample; at least one foil cover sealing the plurality of compartments; and an ejection mechanism adapted to eject one of the plurality of test sensors from the linear cartridge, the ejection mechanism including: a lever pivotally coupled to the housing, the lever being movable between a first position substantially parallel to the longitudinal axis and a second position substantially perpendicular to the longitudinal axis; a blade associated with the lever, the blade being movable between a first position, where no portion of the blade is located, within at least one compartment of the plurality of compartments, and a second position, where at least a portion of the blade is positioned within at least one compartment of the plurality of compartments to open one compartment at a time. The blade may be slidably mounted in the lever.

BRIEF DESCRIPTION OF THE DRAWINGS

Various embodiments of the present invention will now be described with reference to the appended drawings. It is appreciated that these drawings depict only some embodiments of the invention and are therefore not to be considered limiting of its scope.

DETAILED DESCRIPTION

Figure 1:
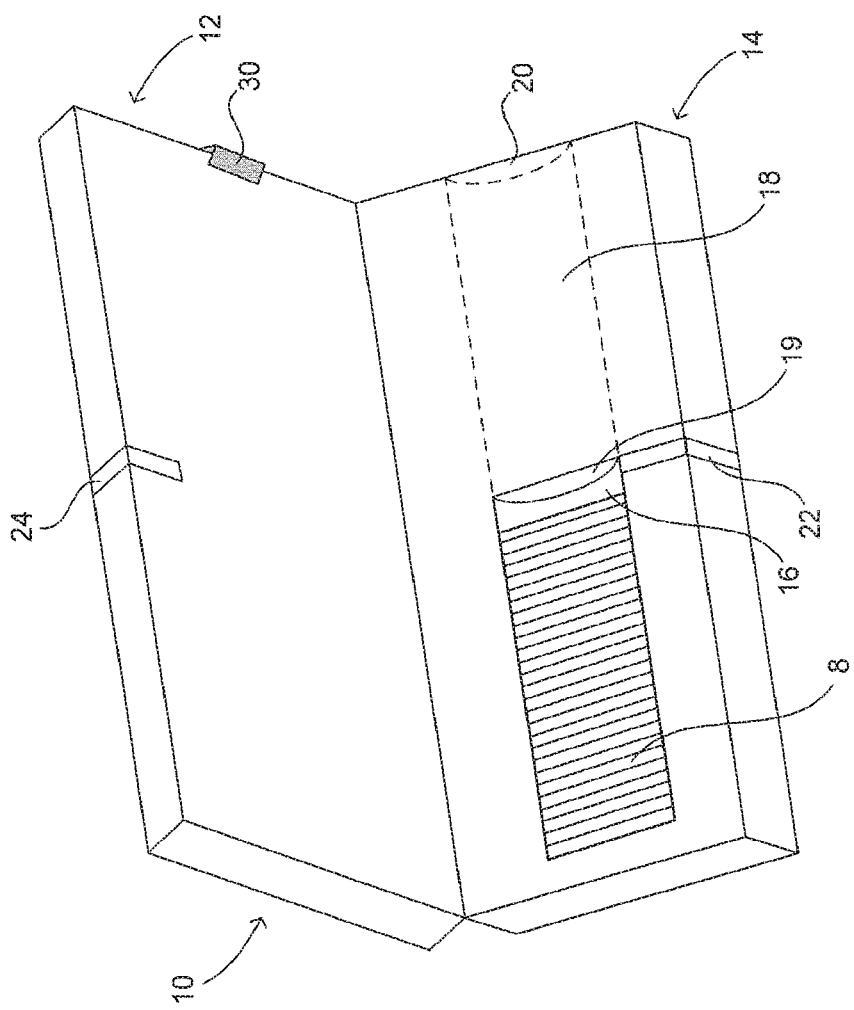
FIG. 1 is a perspective view of an analyte meter in accordance with one embodiment of the present invention in an open condition.
Figure 2:
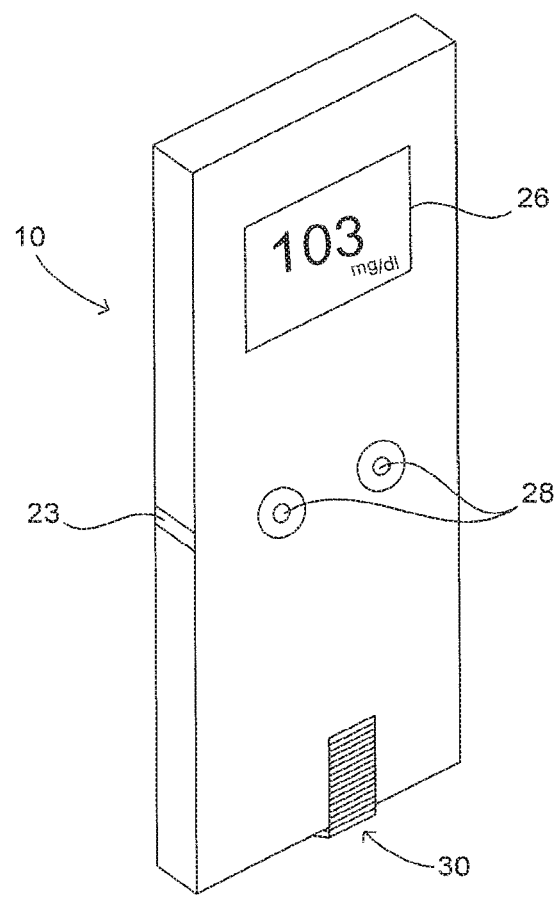
FIG. 2 is a perspective view of the analyte meter of FIG. 1 in a closed condition.

FIGS. 1 and 2 show an embodiment of an analyte meter 10 designed to determine and measure the presence and/or concentration of an analyte (e.g., blood glucose) in a fluid sample. FIG. 1 shows analyte meter 10 in an open condition, while FIG. 2 depicts analyte meter 10 in a closed condition. As seen in FIG. 1, analyte meter 10 includes a top portion 12 and a bottom portion 14 pivotally coupled to each other. A hinge or any other suitable mechanism pivotally connects the top portion 12 and the bottom portion 14 along one of its edges. The bottom portion 14 of the analyte meter 10 defines an internal cavity 16 configured and dimensioned to hold linear cartridge S. As discussed in detail below, the linear cartridge 8 can hold a plurality of test sensor or strips. In addition to cavity 16, the bottom portion 14 of the analyte member 10 may include a track or channel 18 configured and dimensioned to receive the linear cartridge 8. Channel 18 has a first open end 18 leading to cavity 16 and a second open end 20 for inserting the linear cartridge S. Aside from channel 18, the bottom portion 14 has a slot 22 in communication with cavity 16. The top portion 12 also has a slot 24, which is in communication with and aligned with slot 22 when analyte meter 10 is in the closed condition. Together, slots 22 and 24 form a test strip port 23 (FIG. 2) adapted and dimensioned to receive at least one test strip. During operation, the test strips are ejected from the analyte meter 10 through test strip port 23.

Figure 3:
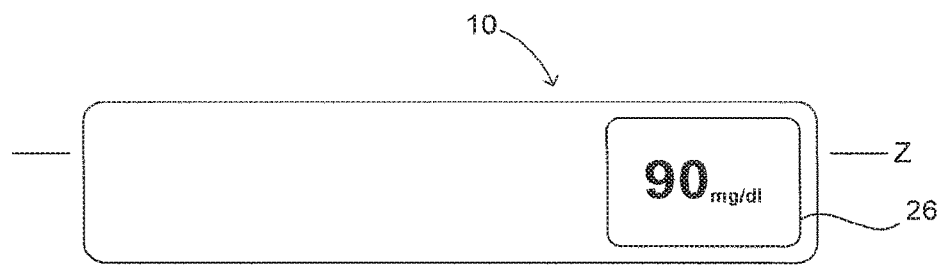
FIG. 3 is a top view of an analyte meter according to another embodiment of the present disclosure.

As seen in FIGS. 2 and 3, analyte meter 10 includes a display unit 26 and associated components for displaying information relevant to the analyte measurement taken by analyte meter 10. For instance, display unit 26 may display the analyte concentration (e.g., blood glucose concentration level) in a fluid sample. Display unit 26 may be a liquid crystal display panel or any other display device capable of depicting images, text or any other type of information, such as color coded images. Analyte meter 10 further includes one or more buttons 28 for ejecting a test strip stored in linear cartridge 8. Aside from buttons 28, analyte member 10 includes an indexing fever 30 for displacing the test strips to the appropriate position after ejecting one test strip.

Figure 4A:
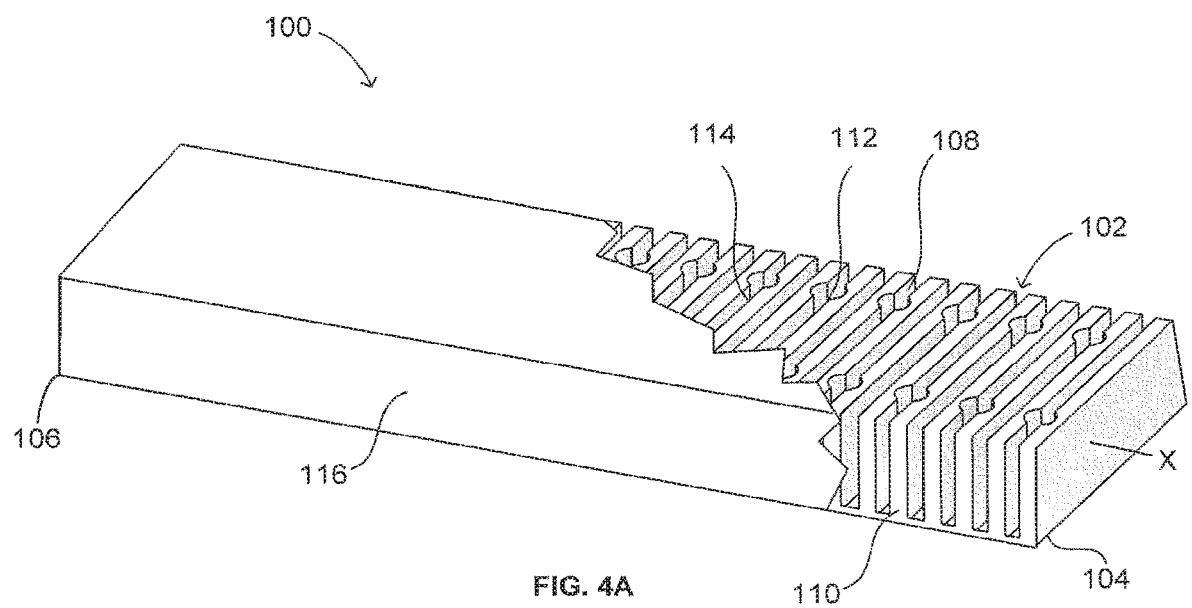
FIG. 4A is a perspective view of a linear cartridge for use with the analyte meter of FIGS. 1 and 3.

FIG. 4A illustrates a linear cartridge 100 for use with analyte meter 10. Linear cartridge 100 can hold a plurality of test sensor or strips, preferably 30 or more. In one embodiment, linear cartridge 100 can hold at least 10 test strips. Each test strip contains a reagent capable of reacting with an analyte (e.g., blood glucose) to produce a measurable signal indicative of the presence and/or concentration of said analyte. In some embodiments, linear cartridge 100 may be made of a substantially rigid material, such as stainless steel or plastic.

Linear cartridge 100 may have a substantially rectangular shape and includes a plurality of compartments or test strip containing regions 102. Compartments 102 are arranged substantially parallel to one another along a longitudinal axis X defined between the first end 104 and the second end 106 of the linear cartridge 100. Each compartment 102 has a slit 108 configured and dimensioned to receive a test sensor or strip. Each slit 108 extends between opposite sidewalls 110 of the linear cartridge 100 and is oriented substantially perpendicular to the longitudinal axis X.

Figure 4B:
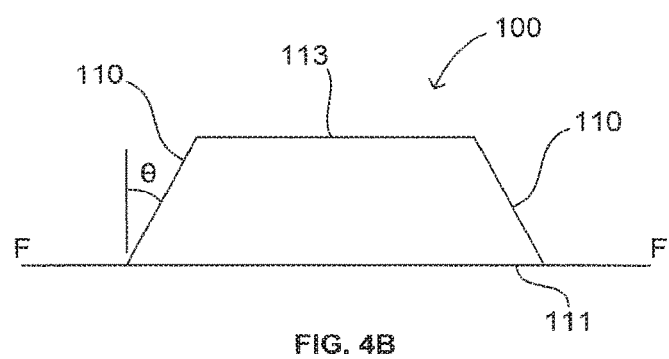
FIG. 4B is a front view of the linear cartridge of FIG. 4A.

As shown in FIG. 4B, linear cartridge 100 has a top portion 113, a bottom portion or base 111, and two opposite side walls 110. Bottom portion 111 is oriented along a longitudinal axis F and may be substantially parallel to the top portion 113. At least one of the sidewalls 110 may be oriented at an angle $\theta$, preferably an acute angle, relative to the vertical axis that is perpendicular to bottom portion 111. As discussed below in detail, the angled sidewalls 110 allow a foil to cover the sidewalls 110 at an angle relative to the test strip positions in a compartment 102. The angled orientation of the foil allows a test strip without angled face to pierce the foil during ejection.

In some embodiments, each compartment 102 has one or more cavities 112 for holding desiccant material. Desiccant material is disposed in cavities 112 to maintain an appropriate humidity level in the compartments 102, thereby avoiding potentially adverse effects on the reagent material in the test sensors or strips. Cavities 112 may have a cylindrical shape and may hold desiccant material shaped as beads. Other suitable arrangements are also contemplated. In some embodiments, each cavity 112 of a compartment 102 is in fluid communication only with a single slit 108 of the same compartment 102.

At least one foil cover 116 is attached to at least the top portion 114 and sidewalls 110 of the linear cartridge 100 to seal and cover each compartment 102. In exemplary assembly methods, the foil cover 116 is hear welded or glued to the linear cartridge 100. While ejecting a test strip, a portion of foil cover 116 adjacent to a compartment 102 is cut to release the test strip. As discussed above, foil cover 116 seals the sidewalls 100 of the linear cartridge 100 at an acute angle relative to the vertical axis perpendicular to bottom portion 111. This angled orientation of foil cover 116 facilitates piercing by the test sensor upon ejection. While the test sensor punctures a portion of foil cover 116 sealing a single compartment 102 during ejection, other portions of foil cover 116 maintain the remaining compartments 102 sealed. In doing so, the remaining test strips are individually protected from the adverse effects of humidity even when one test strip is ejected from the linear cartridge 100. In other words, the foil cover seals each compartment 102 individually. This eliminates the need for a robust reversible seal that would seal each of the strips in unison. The compartments 102 of linear cartridge 100 can be maintained at the appropriate humidity level even when another compartment 102 is opened. Thus, opening one compartment 102 of the linear cartridge 100 may not affect another compartment 102. Alternatively or additionally, linear cartridge 100 may be made or molded from a desiccant-containing resin.

Figure 5:
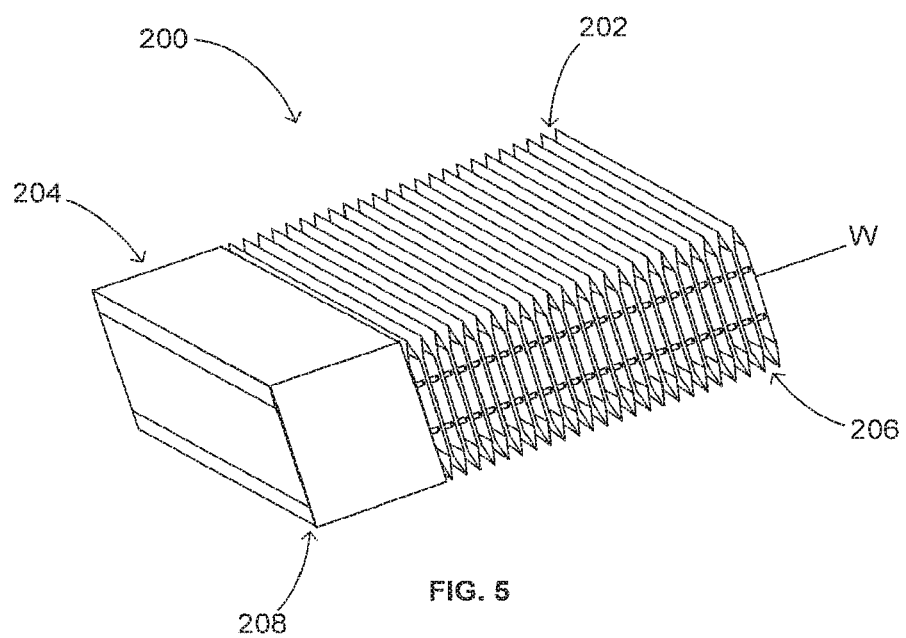
FIG. 5 is a perspective view of a linear cartridge according to another embodiment of the present disclosure.

FIG. 5 depicts a collapsible linear cartridge 200 for storing a plurality of test sensors or strips. Linear cartridge 200 includes a plurality of compartments or test sensor containing regions 202 each configured and dimensioned to hold a test sensor strip. In some embodiments, linear cartridge 200 may include between 25 and 75 compartments 202. For example, linear cartridge may include 50 compartments 202. Nonetheless, linear cartridge 200 may include more or fewer compartments 202. Irrespective of the exact number of compartments 202, each compartment 202 may be made of a flexible and/or collapsible material. The compartments 202 are connected to one another in an accordion-style fashion along a longitudinal axis W between a first end 206 and a second end 208 of the linear cartridge 200. In addition to the compartments 202, linear cartridge 200 includes a housing 204 at its second end 208. Housing 204 may be made of a substantially rigid material and may support at least some compartments 202.

Figure 6:
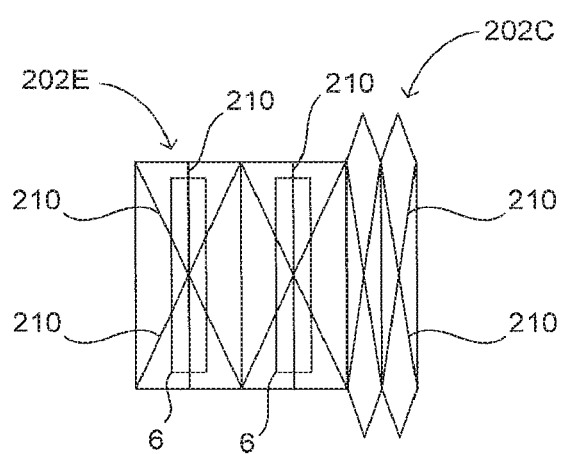
FIG. 6 is an enlarged side view of a portion of the linear cartridge of FIG. 5.

As seen in FIG. 6, each compartment 202 can be reconfigured between an expanded state and a collapsed state. In the expanded state, each compartment 202e is adapted and dimensioned to surround and hold a test strip 6. When the test strip 6 is ejected from a compartment 202e, the compartment 202e can be collapsed. In the collapsed state, compartment 202c has a flattened configuration and occupies less space than in the expanded state. To facilitate this reconfiguration from the expanded state to the collapsed state, each compartment 202 may include one or more folding lines 210. In the embodiment depicted in FIG. 6, each compartment 202 includes two folding lines 210 oriented diagonally relative to each other and another folding line 210 crossing the two diagonal folding lines at the same location. Accordingly, compartments 202 can fold along the folding lines 210 when moving between the expanded state and the collapsed state.

Figure 10:
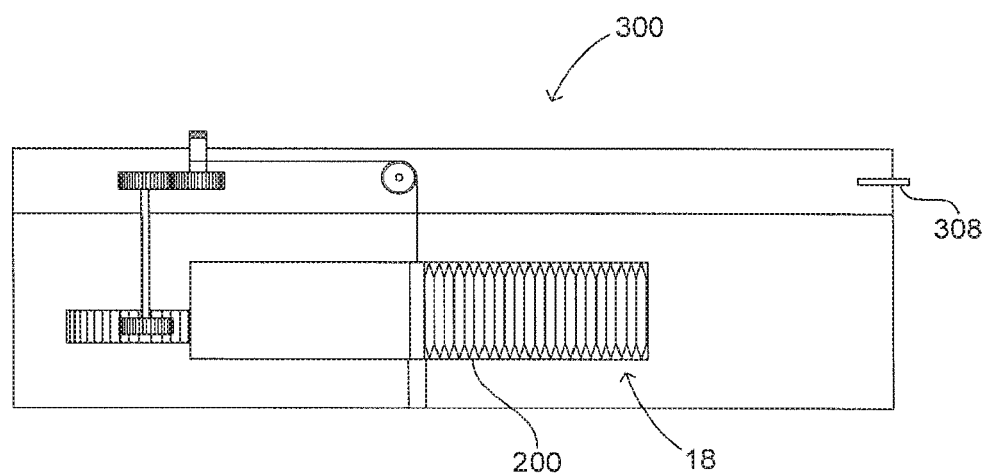
FIG. 10 is a cross-sectional side view of the analyte meter of FIG. 7 holding the linear cartridge of FIG. 5 in the collapsed condition.

The collapsibility of the compartments 202 allows linear cartridge 200 to be placed in an analyte meter with a footprint or length smaller than in conventional meters. As seen in FIG. 1, some analyte meters have a channel 18 dimensioned to receive substantially the entire length of a linear cartridge (e.g., cartridge 8). After ejecting a single test trip from one compartment of the cartridge 8, the user usually displaces the cartridge 8 toward the open end 20 of channel 18 to position the next compartment next to slot 22. The user may then sequentially eject the test strips contained in the compartments of the cartridge until the only one test strips remains. At this point, substantially the entire length of the cartridge 8 is positioned within channel 18. Accordingly, channel 18 should be dimensioned to accommodate substantially the entire length of the cartridge 8. If, however, the linear cartridge 200 is employed with the analyte meter, the channel 18 of the meter only has to be dimensioned to receive the linear cartridge 200 in the collapsed condition, as seen in FIG. 10. As discussed above, each compartment 202 of the linear cartridge 200 can collapse after the test strip has been ejected therefrom. Accordingly, the length of linear cartridge 200 between the first end 206 and the second end 208 defined along axis hi is shorten when at least one compartment 202 is in the collapsed condition than when almost all compartments 202 are in the expanded condition. As such, the channel 18 of the analyte meter only needs to be dimensioned to accommodate the linear cartridge 200 when all the compartments 202 are in the collapsed condition. Therefore, the analyte meter may have a shorter length than conventional meters.

Linear cartridge 200 may be used to hold very stable test sensors or strips 6 that do not require desiccation. Alternatively, linear cartridge 200 may hold test sensors 6 having a molded-in desiccant sheet as one of the sensor layers. In any event, each compartment 202 is individually sealed with foil cover, either in one continuous sheet or as separate sheets.

Figure 7:
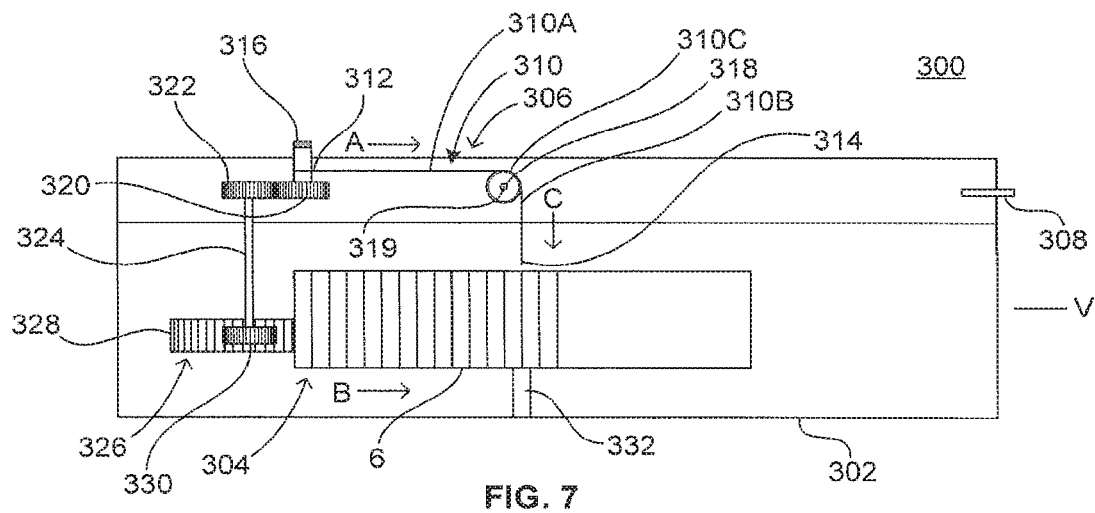
FIG. 7 is a cross-sectional side view of an analyte meter with a flexible sensor ejection blade.

FIG. 7 illustrates another embodiment of an analyte meter 300 for detecting and measuring analytes in a fluid sample. Analyte meter 300 includes a housing 302 for holding any suitable linear cartridge (e.g., linear cartridges 100 or 200.) and a processor for evaluating the signal received from test strips. Housing 302 includes an internal cavity 304 adapted and dimensioned to receive the linear cartridge. The linear cartridge can hold a plurality of test sensor or strips 6. Each test trip includes electrodes for transmitting electrical signals indicative of the presence and/or concentration of an analyte to the processor of the analyte meter 300. Analyte meter 300 also includes electrodes electrically linked to the process for transmitting the electrical signals generated by the test strips. The electrodes of the analyte meter and the electrodes of the aligned with one another when the test strip has been ejected from the linear cartridge 100. When these electrodes are aligned, the electrical signals generated by the test strips can be transmitted to the processor. The processor then analyzes these signals and displays the results (e.g., analyte concentration level) to the user via a display device.

Analyte meter 300 may further include a lancing mechanism 308 and an ejection mechanism 306 for ejecting test sensor or strips 6. Although the lancing mechanism 308 is shown partially exterior to the housing 302, it is noted that this is a deployed use position. For storage, the lancing mechanism 308 may be completely within the housing 302 or may be removed altogether.

Ejection mechanism 306 is configured to eject at least one test strip 6 from the linear cartridge stored within housing 302 through port 332. In some embodiments, ejection mechanism 306 includes an ejection blade 310 dimensioned to be inserted in one compartment of the linear cartridge. Ejection blade 310 is made partly or entirely of a flexible material, or may be configured from a rigid material with one or more joints. For example, ejection blade 310 may be formed of a flexible metal band. A first end 312 of the ejection blade 310 is operatively connected to an ejection button 316, whereas a second end 314 is free (i.e., not connected to any other structure). As will be discussed below, the ejection button 316 is moveable between a first position and a second position to eject a test strip and rotatable to advance the linear cartridge within the housing 402. A portion 310c of ejection blade 310 is positioned over a spindle 318 rotatably coupled to housing 302. A rod or pin 319 may rotatably connect spindle 318 to housing 302. Though spindle 318 can rotate, it is otherwise fixed to the housing 302. Spindle 318 is configured to rotate to direct the movement of ejection blade 310, as discussed in detail below. When spindle 318 is stationary (i.e., not rotating), it divides ejection blade 318 into two portions, namely, a first portion 310a and a second portion 310b. The first portion 310a of the ejection blade 310 is oriented substantially parallel to the longitudinal axis V defined by housing 302, whereas the second portion 310b of the ejection blade 318 is oriented substantially orthogonal to the longitudinal axis V to orient the second portion 310b with port 332. It will be appreciated that the first portion 310a and second portion 310b may travel along other paths, which may not be substantially orthogonal to each other. For example, the second portion 310b may extend at an obtuse angle from the first portion 310a, in such cases, it is preferred that port 332 extends along a corresponding axis.

As discussed above, the first end 312 of the ejection blade 310 is attached to the ejection button 316. Consequently, ejection button 316 is adapted to move longitudinally to displace at least the first portion 310a of the ejection blade 310 in the direction indicated by arrow A. Specifically, ejection button 316 can move between a first position and a second position. When ejection button 316 is moved from the first position to the second position, at least a portion of ejection blade 310 moves longitudinally in the direction indicated by arrow A. As ejection blade 310 moves longitudinally, spindle 318 rotates about pin 319 and directs the second portion 310b of ejection blade 310 toward the linear cartridge in the direction indicated by arrow C.

Ejection button 316 is rotatably coupled to a first gear 320. Consequently, rotating button 316 causes the first gear 320 to rotate. First gear 320 is configured to mesh with a second gear 322 when the ejection button 316 is in the first position. Thus, when the ejection button 316 is in the first position, rotating the first gear 320 causes the rotation of the second gear 322. Second gear 322 rotatably drives a shaft or rod 324, such that rotating the second gear 322 results in the rotation of the shaft 324. Shaft 324 is coupled to an advancing mechanism 326 for advancing the linear cartridge in the direction indicated by arrow B upon rotation of ejection button 316 when in the first position. In one embodiment, advancing mechanism 326 includes a rack 328 and pinion 330 adapted to mesh with one another. Pinion 330 is rotatably connected to shaft 324, so that the rotation of shaft 324 causes the rotation of pinion 330. In turn, the rotation of pinion 330 causes the rack 328 to move longitudinally. As rack 328 moves longitudinally, it pushes the linear cartridge, thereby advancing the cartridge in the direction indicated by arrow B. Although FIG. 7 shows rack 328 and pinion 330, analyte meter 300 may alternatively include any other advancing mechanism capable of displacing the linear cartridge in a longitudinally direction by converting rotational movement of the ejection button 316 into translational movement of the linear cartridge 200.

In operation, the ejection mechanism 306 of analyte meter 300 can be employed to eject a test strip 6 from the linear cartridge. To eject a test strip 6, the user first moves ejection button 316 from the first position to the second position in the direction indicated by arrow A (the second position being toward the spindle 318). As ejection button 316 moves longitudinally, at least the first portion 310a of the election blade 310 moves longitudinally in the direction indicated by arrow A. While the first portion 310a of the ejection blade 310 moves longitudinally, spindle 318 rotates and directs at least the second Portion 310b of the election blade 310 toward the linear cartridge. Specifically, the second portion 310b moves in the direction indicated by arrow C upon rotation of spindle 313. The second portion 310b of the ejection blade 310 eventually pierces a portion of the foil covering one compartment of the linear cartridge and pushes the test strip 6 stored inside that compartment through the port 332.

After ejecting a test strip 6, the user moves the ejection button 316 from the second position to the first position. When ejection button 316 is in the first position, the first gear 320 is operatively engaged to the second gear 322. At this point, the user turns the ejection button 316 to rotate the first gear 320. The rotation of the first gear 320 causes the second gear 322 to rotate. Shaft 324 rotates concomitantly with the second gear 322. The rotating shaft 324 drives the pinion 330. As pinion 330 rotates, it urges rack 328 to move longitudinally in the direction indicated by arrow B. The longitudinal motion of rack 328 moves the linear cartridge at least one position along the cavity 304 to align the next test strip 6 with port 332 in anticipation of its ejection.

Figure 8:
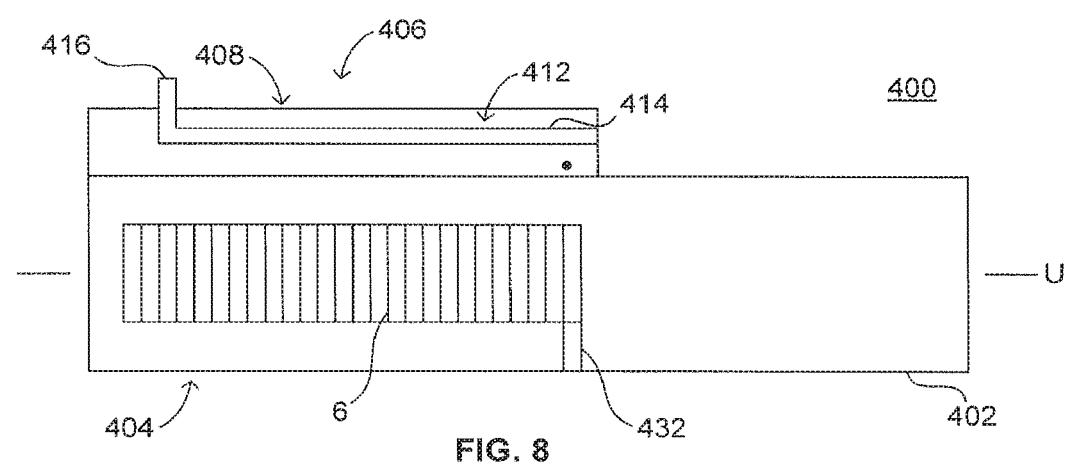
FIG. 8 is a cross-sectional side view of an analyte meter with a pivotable ejection mechanism in a first position.
Figure 9:
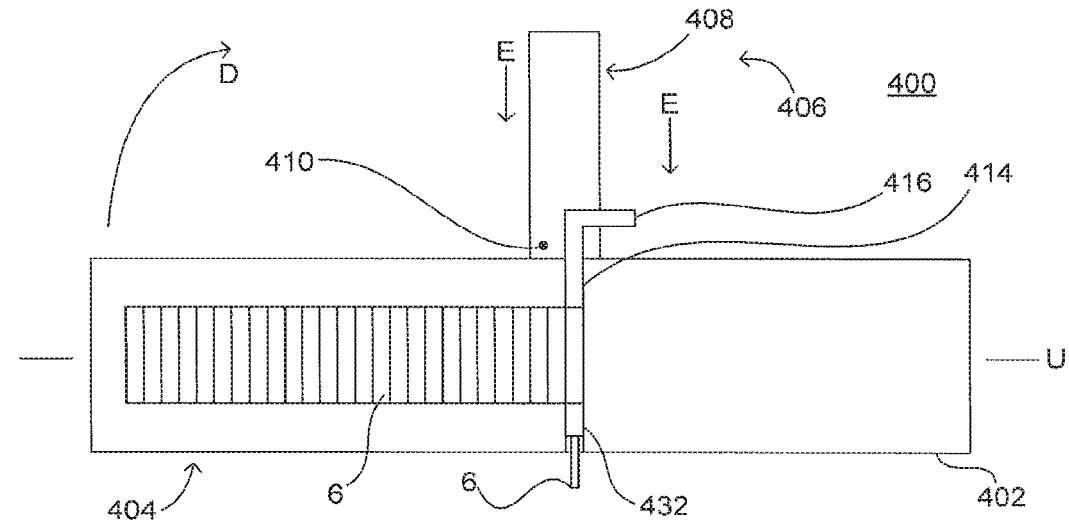
FIG. 9 is a cross-sectional side view of the analyte meter of FIG. 8 in a second position.

FIGS. 8 and 9 show another embodiment of an analyte meter 400 for sensing and measuring analytes in a fluid sample. Analyte meter 400 includes a processor for analyzing electrical signals and housing 402 for holding a linear cartridge (e.g., linear cartridges 100 or 200). Housing 402 has an internal cavity 404 adapted and dimensioned to receive the linear cartridge. The linear cartridge has individual compartments each configured to hold a test sensor or strip 6. These compartments are individually sealed with a foil cover. Each test sensor includes electrodes for transmitting electrical signals indicative of the presence and/or concentration of an analyte in a fluid sample to the processor. Analyte meter 400 further includes electrodes electrically linked to the processor. These electrodes transmit the electrical signals generated by the test strips to the processor. The electrodes of the analyte meter and the electrodes of the aligned with one another when the test strip has been ejected from the linear cartridge 100. When these electrodes are aligned, the electrical signals generated by the test strips can be transmitted to the processor. The processor then analyzes these signals and displays the results (e.g., analyte concentration level) to the user via a display device.

Analyte meter 400 further includes an ejection mechanism 406 for ejecting a test sensor 6 from a compartment of the linear cartridge. Ejection mechanism 406 includes a lever 408 pivotally coupled to housing 402. Accordingly, lever 408 can pivot relative to housing 402 between a first position (FIG. 8) and a second position (FIG. 9). In the first position, lever 408 is oriented substantially parallel to the longitudinal axis U defined by housing 402. In the second position, lever 408 is oriented substantially perpendicular to the longitudinal axis U. A hinge 410, a pivot pin, or any other suitable means pivotally connects the lever 408 to housing 402. Lever 408 includes a slot 412 adapted and dimensioned for receiving an ejection blade 414. Ejection blade 414 may be made of a substantially rigid material and is slidably positioned in the slot 412 of lever 408. Thus, ejection blade 414 can move along slot 412 between a first position (FIG. 8) and a second position (FIG. 9) via an election button 416. Ejection button 416 is operatively connected to ejection blade 414 and is preferably configured to be handled and moved by a human hand. In operation, a user can move ejection button 416 to slide ejection blade 414 along slot 412. Ejection blade 416 is adapted pierce a foil sealing a compartment of the linear cartridge. Moreover, ejection blade 416 is configured and dimensioned to be inserted into the compartment of the linear cartridge to push the test sensor stored in that compartment through port 432.

In operation, ejection mechanism 406 can be employed to eject a test sensor scored in the linear cartridge. To do so, the user first pivots lever 408 from the first position, as shown in FIG. 8, to the second position, as shown in FIG. 9, in the direction indicated by arrow D. Once the lever 408 is in the second position, the user moves the ejection button 416 in the direction indicated by arrow E to move the ejection blade 414 from the first position to the second position. The ejection blade 414 travels and pierces the foil sealing a compartment of the linear cartridge and then pushes the test sensor 6 stored in that compartment, thereby ejecting the test sensor 6 from the linear cartridge through a port 432, as shown in FIG. 9. Analyte meter 400 may include a suitable advancing mechanism, such as the advancing mechanism 326 shown in FIG. 7, for moving the linear cartridge at least one position along the cavity 404 to align the next test strip 6 with port 432 in anticipation of its ejection.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended embodiments.

What is claimed is:

1. A test sensor container for use with an analyte measuring system, comprising:
a cartridge including a base, a top portion, two opposite sidewalls extending from the base to the top portion, and a plurality of compartments arranged linearly along a longitudinal axis, wherein each compartment is dimensioned to hold a test sensor, and at least one of the two opposite sidewalls is entirely linear forming a straight line from the base to the top portion and oriented at an acute angle relative to a reference axis perpendicular to the base;
at least one foil cover sealing the plurality of compartments; and
an ejection mechanism adjacent the cartridge and configured to eject a test sensor from the cartridge by causing the test sensor to pierce the at least one foil cover at the at least one of the two opposite sidewalls to create an opening through which the test sensor is ejected.

2. The test sensor container of claim 1, wherein the at least one foil cover comprises a single foil cover.

3. The test sensor container of claim 1, wherein the plurality of compartments extends between the two opposite sidewalls.

4. The test sensor container of claim 1, wherein the at least one foil cover extends over the two opposite sidewalls.

5. The test sensor container of claim 1, wherein the two opposite sidewalls are each oriented at an acute angle relative to the reference axis perpendicular to the base.

6. The test sensor container of claim 1, further comprising a plurality of test sensors stored respectively in the plurality of compartments and arranged side by side along a length of the cartridge extending along the longitudinal axis.

7. The test sensor container of claim 6, wherein each of the plurality of test sensors has a side extending parallel to the reference axis and adjacent the at least one of the two opposite sidewalls oriented at the acute angle.

8. The test sensor container of claim 7, wherein the ejection mechanism comprises an ejection blade configured to push one of the plurality of test sensors such that the side extending parallel to the reference axis pierces the at least one foil cover at the at least one of the two opposite sidewalls oriented at the acute angle.

9. The test sensor container of claim 1, wherein each compartment of the plurality of compartments comprises a cavity for receiving a desiccant material therein.

10. The test sensor container of claim 1, wherein the ejection mechanism is further configured to pierce a first portion of the at least one foil cover at the other of the two opposite sidewalls to open only one of the plurality of compartments at a time without opening any other one of the plurality of compartments and to move through the only one compartment toward the one of the two opposite sidewalls.

11. The test sensor container of claim 10, wherein the ejection mechanism comprises a flexible blade movable between a first blade position and a second blade position, wherein no portion of the flexible blade is located within any one of the plurality of compartments in the first blade position, and at least a portion of the flexible blade is located within one of the plurality of compartments in the second blade position, the flexible blade piercing the first portion of the at least one foil cover as a result of moving from the first blade position to the second blade position.

12. The test sensor container of claim 11, wherein the ejection mechanism further comprises an ejection button configured to move the flexible blade, the flexible blade having a first end and a second end, the first end connected to the ejection button and the second end not connected to any structure.

13. The test sensor container of claim 11, wherein the ejection mechanism further comprises a rotatable spindle about which the flexible blade has a first blade portion extending in a first direction and a second blade portion extending in a second direction.

14. The test sensor container of claim 13, wherein the second blade portion is substantially perpendicular to the first blade portion.

15. The test sensor container of claim 13, further comprising an ejection port configured to receive there through the test sensor, wherein the second blade portion is aligned with the ejection port.

16. A test sensor container for use with an analyte measuring system, comprising:
a cartridge including a base, two opposite sidewalls extending away from the base, and a plurality of compartments arranged linearly along a longitudinal axis, wherein each compartment is dimensioned to hold a test sensor, and at least one of the two opposite sidewalls is oriented at an acute angle relative to a reference axis perpendicular to the base;
at least one foil cover sealing the plurality of compartments;
an ejection mechanism adjacent the cartridge and configured to break a first portion of the at least one foil cover at one of the two opposite sidewalls to open only one of the plurality of compartments at a time without opening any other one of the plurality of compartments; and
a housing having the cartridge therein, wherein the ejection mechanism comprises:
a lever pivotally coupled to the housing, the lever movable from a first lever position substantially parallel to the longitudinal axis to a second lever position substantially perpendicular to the longitudinal axis; and
an ejection blade mounted to the lever and movable between a first blade position and a second blade position, wherein no portion of the ejection blade is located within any one of the plurality of compartments in the first blade position, and at least a portion of the ejection blade is located within one of the plurality of compartments in the second blade position, the ejection blade breaking the first portion of the at least one foil cover as a result of moving from the first blade position to the second blade position.

17. The test sensor container of claim 16, wherein the ejection blade is slidably mounted to the lever.

18. The test sensor container of claim 16, wherein the ejection blade is movable linearly between the first blade position and the second blade position.

19. The test sensor container of claim 16, wherein the ejection blade is movable substantially perpendicular to the longitudinal axis from the first blade position to the second blade position.

20. The test sensor container of claim 16, wherein the ejection blade is made of a substantially rigid material.

* * * * *